United States Patent [19]

Gregory

[11] Patent Number: 5,573,531
[45] Date of Patent: Nov. 12, 1996

[54] FLUID CORE LASER ANGIOSCOPE

[76] Inventor: Kenton W. Gregory, 9155 SW. Barnes Rd., Suite 204, Portland, Oreg. 97225

[21] Appl. No.: 262,926

[22] Filed: Jun. 20, 1994

[51] Int. Cl.$^6$ .................................................. A61B 17/36
[52] U.S. Cl. ................................ 606/14; 606/15; 606/16; 606/7; 600/108; 385/125
[58] Field of Search ........................... 606/7, 13, 14–17; 128/4, 6; 607/88, 89; 600/108; 385/125

[56] References Cited

U.S. PATENT DOCUMENTS

| | | | |
|---|---|---|---|
| 3,995,934 | 12/1976 | Nath | 385/125 |
| 4,045,119 | 8/1977 | Eastgate | 385/125 |
| 4,201,446 | 5/1980 | Geddes et al. | 385/125 |
| 4,697,870 | 10/1987 | Richards | 385/125 |
| 4,848,336 | 7/1989 | Fox et al. | 606/7 |
| 4,927,231 | 5/1990 | Levatter | 385/125 |
| 5,187,572 | 2/1993 | Nakamura et al. | 128/6 |
| 5,188,632 | 2/1993 | Goldenberg | 606/7 |
| 5,217,454 | 6/1993 | Khoury | 606/14 X |
| 5,267,341 | 11/1993 | Shearin | 606/15 |
| 5,304,171 | 4/1994 | Gregory et al. | 606/7 X |

FOREIGN PATENT DOCUMENTS 247746  12/1987  European Pat. Off. ................. 606/14

OTHER PUBLICATIONS

King, Spencer B. III, M.D., Douglas John S., Jr., M.D. *Coronory Arteriography and Angioplasty*, Chapter 6, Coronary Arteriography and Left Ventriculographjy: Sones Technique pp. 141–143, 146, 147, 150–154, Copyright 1985, McGraw Hill Book Company.

Sivak, Michael V., Jr., M.D., *Gastroenterologic Endoscopy*, pp. 28–31, Copyright 1987, W.B. Saunders Company.

*Primary Examiner*—Angela D. Sykes
*Assistant Examiner*—Michael Peffley
*Attorney, Agent, or Firm*—Marger, Johnson, McCollom & Stolowitz, P.C.

[57] ABSTRACT

A liquid core laser optical scope for illuminating, viewing, and delivering laser energy to a site in a lumen of an animal or human body which includes a flexible tube for insertion into the lumen, a conduit housed within the tube, a fluid source for coupling a flow of light transmissive liquid into the conduit, a light source for transmitting visible light through the tube to illuminate the site, an optical fiber bundle having an optical receiving end disposed at the distal end of the optical scope for imaging the illuminated site and transmitting a visible image thereof through the optical scope to an external viewing port, and a fluid core light guide for transmitting laser energy from an energy source into the conduit where the conduit has a sidewall capable of internally reflecting light into the liquid in the conduit so that the liquid waveguides the laser energy through the conduit to the site. The fluid core light guide serves not only to couple laser energy to the site in the lumen but to transmit illumination light to the site and reflected images back to the viewing port.

20 Claims, 3 Drawing Sheets

FLUID CORE LASER ANGIOSCOPE

BACKGROUND OF THE INVENTION

1. Field of the Invention

The present invention relates to a method and apparatus for direct visualization and delivery of laser energy to a site that is difficult or inaccessible to reach. In particular, this invention relates to a method and apparatus for visualizing and delivering laser energy to site in a body passage.

2. Description of Related Art

Atherosclerosis, which is a major cause of cardiovascular disease, resulting in heart attacks, is characterized by the progressive accumulation of fatty deposits, known as plaque, on the inner walls of the arteries. As a result, blood flow is restricted and there is an increased likelihood of clot formation that can partially or completely block or occlude an artery, causing a heart attack. Arteries narrowed by atherosclerosis that cannot be treated effectively by drug therapy are typically treated by medical procedures designed to increase blood flow, including highly invasive procedures such as coronary artery bypass surgery and less invasive procedures such as balloon angioplasty, atherectomy and laser angioplasty.

Bypass surgery involves opening the patient's chest and transferring a vein cut from the patient's leg to the heart to construct a detour around the occluded artery. Bypass surgery requires prolonged hospitalization and an extensive recuperation period. Furthermore, bypass surgery also exposes the patient to a risk of major surgical complications.

Balloon angioplasty is a less invasive and less costly alternative to bypass surgery and is performed in a hospital cardiac catheterization laboratory by an interventional cardiologist. In this procedure, a balloon-tipped catheter is inserted into a blood vessel through a small incision in the patient's arm or leg. The physician uses a guide catheter to feed the balloon through the patient's blood vessels to the occluded artery. At that point, a guidewire is inserted across the deposits of atherosclerotic plaque, known as lesions, to provide a pathway for the balloon catheter. The deflated balloon is advanced over the guidewire, positioned within the occluded area and inflated and deflated several times. This inflation and deflation usually tears the plaque and expands the artery beyond its point of elastic recoil. Thus, although no plaque is removed, the opening through which blood flows is enlarged.

Atherectomy employs a rotating mechanical device mounted on a catheter to cut and remove plaque from a diseased artery. Although atherectomy, unlike balloon angioplasty, removes plaque from coronary arteries, existing atherectomy devices are not effective in treating certain types of lesions.

Laser angioplasty removes plaques by using light, in varying wavelengths ranging from ultraviolet to infrared, that is delivered to the lesion by a fiberoptic catheter. Early attempts to develop a laser angioplasty system used continuous wave thermal lasers that generated heat to vaporize plaque. These laser systems caused charring and significant thermal damage to healthy tissue surrounding the lesion. As a result, thermal laser systems have generally been regarded as inappropriate for use in the coronary arteries. In contrast, excimer lasers use ultraviolet light to break the molecular bonds of atherosclerotic plaque, a process known as photoablation. Excimer lasers use electrically excited xenon and chloride gases to generate an ultraviolet laser pulse with a wavelength of 308 nanometers. This wavelength of ultraviolet light is absorbed by the proteins and lipids that comprise plaque, resulting in precise ablation of plaque and the restoration of blood flow without significant thermal or acoustic damage to surrounding tissue. The ablated plaque is converted into carbon dioxide and other gases and minute particulate matter that can be easily eliminated by the body's circulatory system.

In laser angioplasty, conventional light guides using fiber optics are used to direct laser energy onto arterial plaque formations to ablate the plaque and remove the occlusion. Individual optically conducting fibers are typically made of fused silica or quartz, and are generally fairly inflexible unless they are very thin. A thin fiber flexible enough to pass through a lumen having curves of small radius, such as through arterial lumens from the femoral or the brachial artery to a coronary artery, typically projects a beam of laser energy of very small effective diameter, capable of producing only a very small opening in the occlusion. Moreover, the energy is attenuated over relatively small distances as it passes within a thin fiber. Small diameter fibers can mechanically perforate vessels when directed against the vessel wall as they are passed within the vessel toward the site.

In order to bring a sufficient quantity of energy from the laser to the plaque, light guides proposed for use in laser angioplasty usually include a number of very thin fibers, each typically about 100 to 200 microns in diameter, bundled together or bound in a tubular matrix about a central lumen, forming a catheter. Laser energy emerging from a small number of fibers bundled together produces lumens of suboptimal diameter which can require subsequent enlargement by, for example, balloon dilation. Such devices do not remove an adequate quantity of matter from the lesion, and their uses are generally limited to providing access for subsequent conventional balloon angioplasty.

Although individual fibers of such small dimensions are flexible enough to negotiate curves of fairly small radius, a bundle of even a few such fibers is less flexible and more costly. Coupling mechanisms for directing laser energy from the source into the individual fibers in a light guide made up of multiple small fibers can be complex. Improper launch of the laser energy into such a light guide can destroy the fibers. The directing of laser energy thus far has been limited to two-dimensional imaging with fluoroscopy. Frequently, it is not possible to distinguish whether the laser catheter is contacting plaque, normal tissue, or thrombus—all of which have very different therapeutic consequences as well as possible adverse side effects.

To facilitate laser angioplasty, optical scopes, known as angioscopes, have been proposed to directly visualize the area to be treated with the laser. Typically, the scope is inserted into the artery or vein through an incision and then periodically advanced to view desired locations along a length of the vessel. The scopes are attached to a viewing port to which an optical image is transmitted to be viewed by the physician.

Thus, it is highly desirable to combine the viewing function of an angioscope with the ability to deliver laser energy to a particular site simultaneously. One such attempt is disclosed in U.S. Pat. No. 4,641,912 to Goldenberg entitled "Excimer Laser Delivery System, Angioscope and Angioplasty System Incorporating the Delivery System and Angioscope." Goldenberg discloses a system which delivers excimer laser energy, by way of an optical fiber having a core of pure silica aided by an angioscope, to the desired target. U.S. Pat. No. 4,848,336 to Fox et al. shows a similar, albeit more complicated system. There are, however, several drawbacks to such a system.

For example, to ablate the target, the optical fiber must actually contact the target. This is undesirable because it may result in mechanical injury to the tissue which can have a deleterious effect upon the vessel wall. Moreover, contact with the tissue will probably obscure the angioscope's viewing of the target and thus render this method ineffective. Additionally, tissue contact with a laser catheter may produce intrinsically poor laser effects through spatial confinement of the ablation products as well as confining or producing a tamped mode where the laser-induced pressure waves or cavitation effects are magnified. This results in shattering or tearing the tissues, causing unwanted and potentially dangerous damage to the vessel wall.

In addition, an optical fiber, which is large enough to transmit sufficient laser energy to the target, may not be flexible enough to be directed through the particular body lumen to the occluded area. Moreover, it is limited to the delivery of ultraviolet Excimer Laser energy, when it is desirable to deliver a wider spectrum of laser energy, such as visible light for laser thrombolysis. And furthermore, it fails to disclose a means for protecting the eye or CCD crystals from the reflected laser light.

European Patent Application No. 87304072.9 to Tohru entitled "Laser Catheter" discloses a fluid core laser catheter. Tohru's laser catheter has several drawbacks. First, a catheter as described by Tohru can only transmit laser energy effectively less than 40 cm. This is because after 40 cm, the laser energy is too attenuated by scattering and bending losses. Second, to abate the target, the distal end of the catheter must actually contact the target. Thus, even if Tohru's catheter could be combined with Goldenberg's device, it would not be operable. The physician could not properly illuminate or view the target. Moreover, Tohru fails to disclose a means for protecting the eye or CCD crystals from reflected laser light.

Gregory et al, in their article "Liquid Core Light Guide for Laser Angioplasty" *IEEE Journal of Quantum Electronics*, Vol. 26, No. 12, December 1990, discloses a fluid core laser. Gregory et al. fail, however, to teach or suggest how their device could be operatively combined with conventional angioscopes, as taught by Goldenberg for example, to overcome the problems discussed above. Accordingly, a need remains for an instrument that avoids the drawbacks of conventional lasers and laser-angioscopes.

SUMMARY OF THE INVENTION

The present invention is a liquid core laser optical scope for illuminating, viewing, and delivering laser energy to a site in a lumen of an animal or a human body. It includes a flexible tube having a distal end for insertion into the lumen, a conduit housed within the catheter, means for coupling a flow of light transmissive liquid from an external source into the conduit, means for transmitting visible light from an external source through the optical scope to its distal end to illuminate the site, means disposed in the distal end of the optical scope, for imaging the illuminated site and transmitting a visible image thereof through the optical scope to an external viewing port, and means for transmitting laser energy from an energy source into the conduit, the conduit having a sidewall capable of internally reflecting light into the liquid in the conduit so that the liquid waveguides the laser energy through the conduit to the site. At the same time, the scope flushes blood from the field of view so that the site can be angiscopically viewed.

A preferred embodiment of the present invention includes a flexible tube having a proximal end and a distal end for insertion into the lumen, a conduit housed within the tube, means for coupling a flow of light transmissive liquid from a liquid source into a proximal end of the conduit for discharge from the distal end thereof, means disposed in the at the proximal end of the conduit for coupling laser energy from an energy source into the conduit, the conduit having a sidewall capable of internally reflecting light into the liquid in the conduit so that a liquid waveguide transmits the laser energy through the conduit to the site, means disposed at the proximal end of the conduit for coupling visible light from an external light source into the conduit so that the liquid directs the light through the conduit to the distal end of the catheter, to illuminate the site, means disposed at the distal end of the catheter for forming an optical image of the illuminated site, means disposed at the proximal end of the catheter for coupling the transmitted image to a viewing apparatus, and means for selectively excluding the laser energy from the optical image transmitted to the proximal end of the catheter. The flexible tube can include a guidewire channel which can further include a means for directing the fluid stream to the site, such as a tip deflector.

Another aspect of the present invention is a method for ablating a site in a lumen, using the liquid-core laser optical scope, which includes inserting the scope into the lumen, visually directing the distal end to the targeted site, transmitting visible light to the site, flowing light transmissive liquid through the conduit, viewing and aiming at the site, and transmitting laser energy through the liquid filled conduit to ablate the site.

Further features of the present invention and preferred modes for implementing them will become apparent from the following detailed description of preferred embodiments of the invention illustrated in the accompanying drawings. The flexible tube can further include a guidewire channel for advancing the catheter to the desired intravascular location using conventional guidewire and guidewire techniques. A means for directing the fluid stream and the imaging optics to the site with a catheter tip deflector apparatus.

The foregoing and other objects, features and advantages of the invention will become more readily apparent from the following detailed description of a preferred embodiment of the invention which proceeds with reference to the accompanying drawings.

DESCRIPTION OF THE ILLUSTRATED EMBODIMENTS

In the following description of preferred embodiments of the invention, a liquid core laser optical scope is described with particular reference to its use in an angioplasty system, in order to facilitate an understanding of the invention and its uses. Those skilled in the art will appreciate that the practical applications of the optical scope are not limited to this single environment. In the medical field, the term optical scope is a generic term which includes medical instruments such as angioscopes for viewing arteries and veins, endoscopes for viewing the gastrointestinal tract, bronchoscopes for viewing bronchial passages, and arthroscopes for viewing joints. The invention has particular utility in viewing and ablating obstructions such as atheromatous plaque, an atheroembolus, thrombus, blood clots, lesions, kidney stones, gall stones, tumors, or polyps. The invention, in its broader aspects, can find utility in any application in which it is desirable to deliver laser energy by means of a liquid core waveguide, such as in an industrial cutting tool or as a surgical tool used in arthroscopy, for example.

Figure 1:
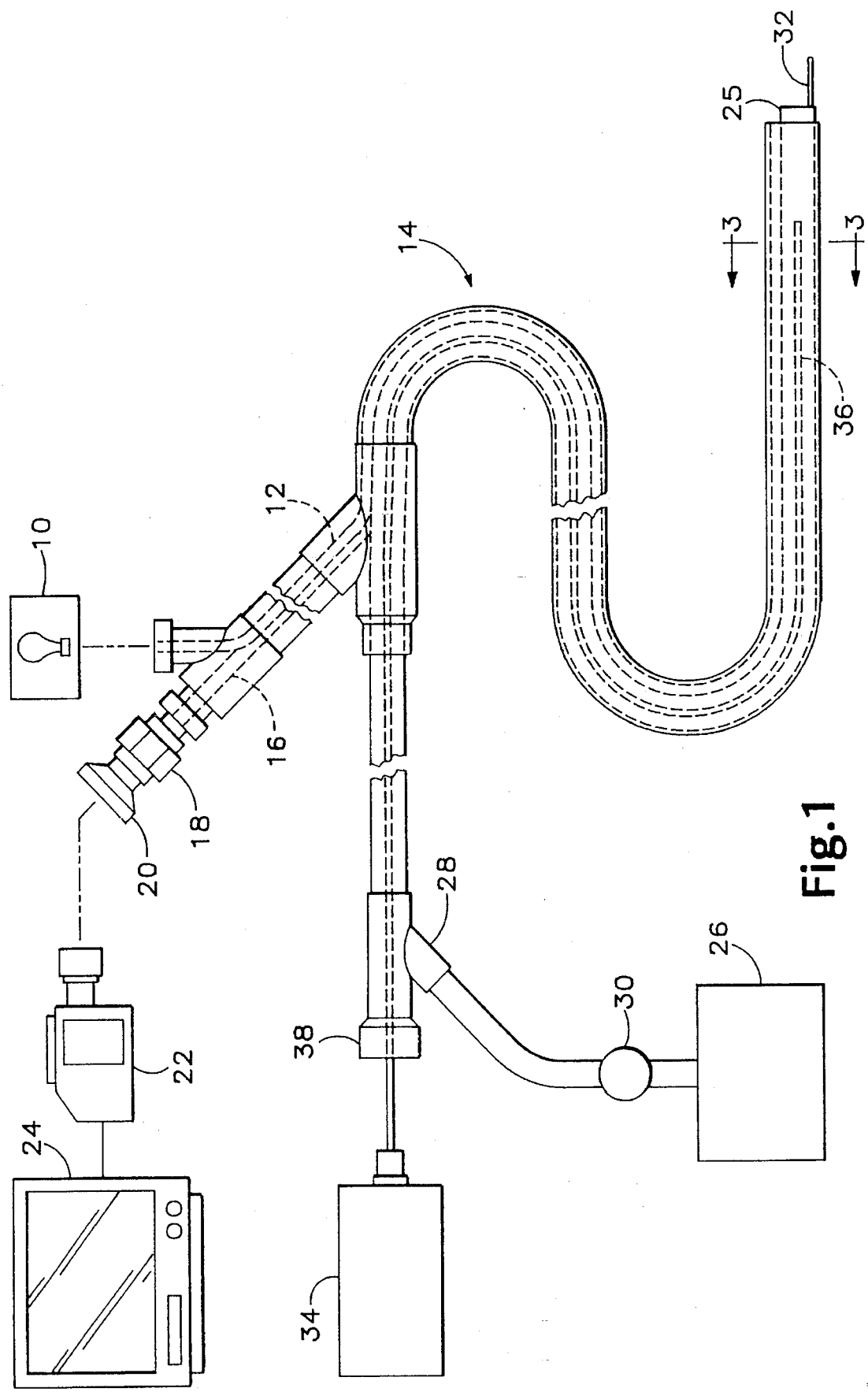
FIG. 1 is a schematic diagram of a laser and image delivery system according to the invention.

Referring to FIG. 1, a system that employs the liquid core laser optical scope of the present invention is shown in schematic form. The laser optical scope must be capable of performing three functions within the lumen. The first two of these relate to the illumination and imaging of the interior of the lumen to enable the scope's operator to successfully propagate the distal end of the system through the lumen to the target. Accordingly, the output from a source of visible light, such as a Halogen or Xenon lamp 10, is directed to the proximal ends of optical fibers 12. The other (distal) end of this fiber is housed within the flexible tube 14 enable it to be fed through the lumen. A coherent bundle of optical fibers 16 located adjacent to optical fibers 12 within the tube receives the image from the illuminated interior of the lumen and transmits it through an excluding means 18 to a viewing port 20 where the image can be monitored by the operator as the flexible tube 14 is being positioned inside the lumen. Alternatively, the image can be transmitted to a video camera 22 which displays the image on the video monitor 24 for viewing by the operator.

Liquid is introduced at the proximal end of the conduit 25 from a liquid source 26. The liquid is discharged into the conduit 25 by way of a liquid discharge means 28. The liquid is coupled into the conduit 25 using a coupling means 30 such as an injector pump or syringe 26.

Once the distal end of the tube 14 has been appropriately positioned adjacent to the target using a guiding means 32, a high energy laser 34, is activated. The energy generated by the laser is coupled into the laser optical fiber 36 by way of a laser coupling means 38. Optical fiber 36 launches the laser energy into the liquid core of conduit 25, which waveguides the laser energy to the distal end of the tube and delivers it to the target.

Figure 2:
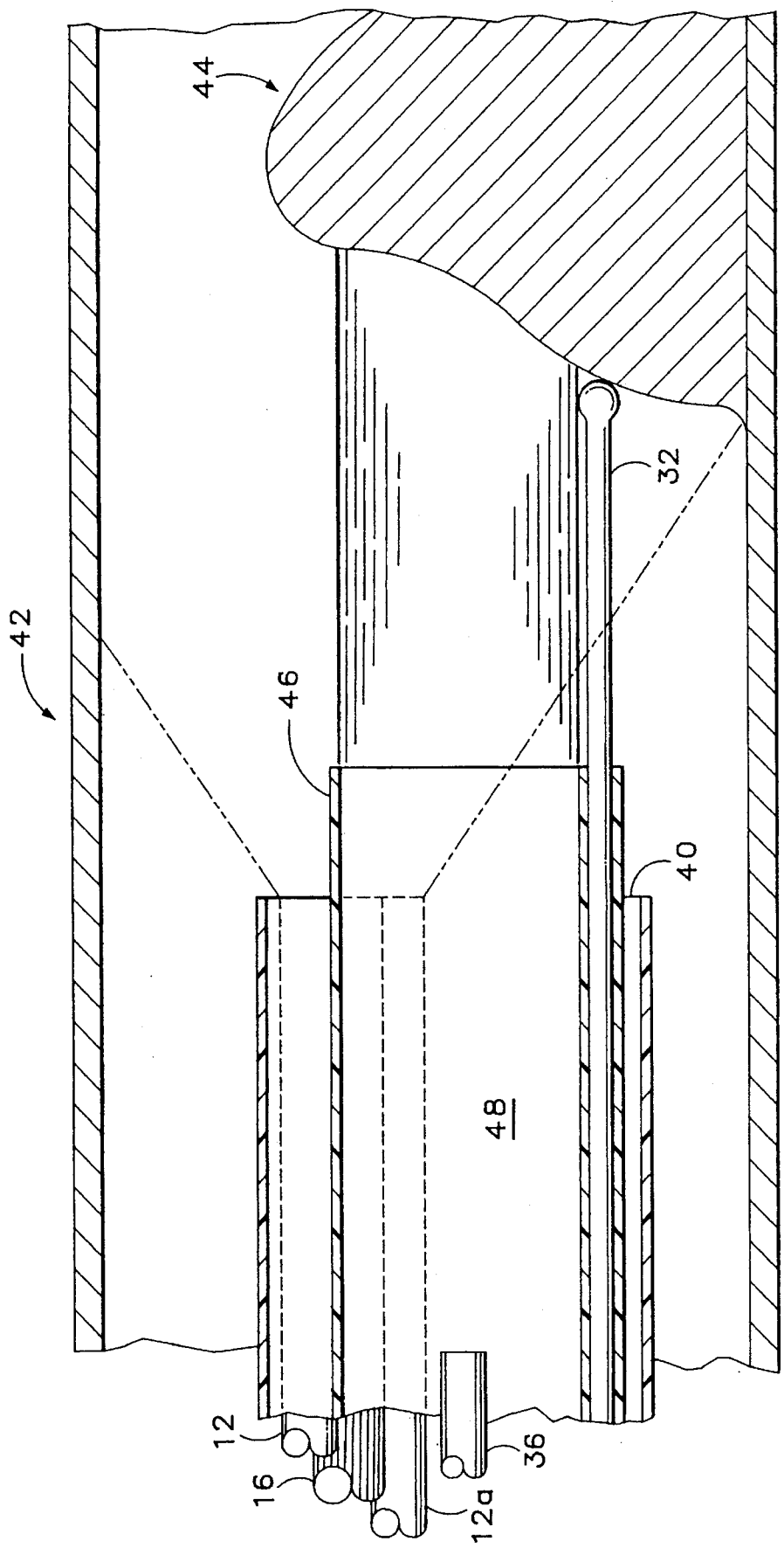
FIG. 2 is a lengthwise sectional view of the distal end portion of the laser optical catheter of FIG. 1, shown in an arterial lumen in proximity to a clot.
Figure 3A:
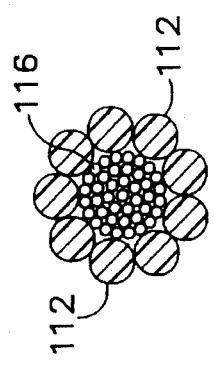
FIG. 3a is a cross-sectional view through the laser optical catheter taken along lines 3—3 at FIG. 1, illustrating an alternative embodiment of the present invention.
Figure 3:
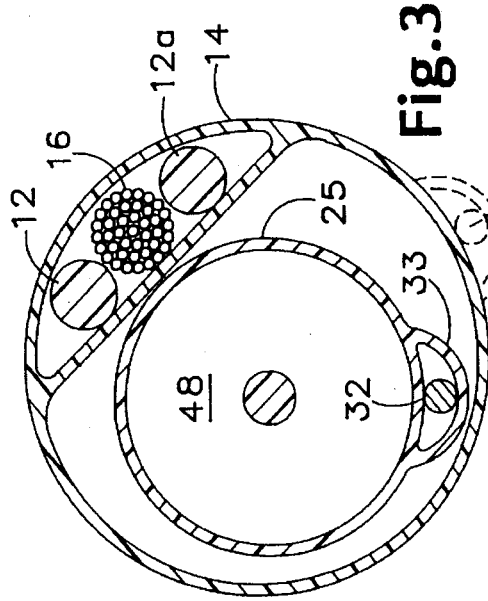
FIG. 3 is a cross-sectional view through the laser optical catheter taken along lines 3—3 at FIG. 1.

Referring now to FIGS. 2 and 3, one embodiment of the present invention will be explained in greater detail. The invention includes a flexible tube 14 having a distal end 40 which is inserted into the lumen. A guidewire 32 guides the distal end to the target 44. The tube encloses a conduit 25 which is filled with a liquid having a suitable index of refraction. The conduit's sidewall defines a lumenal surface and has a suitably low index of refraction compared to the optical fluid to allow internal reflection of light through which the liquid flows.

Once the distal end 40 is positioned adjacent the target 44, laser energy can be directed from a source of laser energy and coupled into the proximal end of optical fiber. Optical fiber 36 launches the laser energy into the liquid. The energy passes within the liquid filled conduit 25 toward distal end 40. The energy is attenuated as it passes away from the energy source, so that a portion of it emerges from the distal end 40. The proportion of the energy introduced into the liquid that emerges from the distal end of the liquid filled conduit 25 depends upon the dimensions and physical characteristics of the liquid and the conduit side wall, and on the extent to which the tube follows a curving course.

One particular application for which the present invention is particularly suited is the field of angioplasty. In such an application, it is desirable to use three additional optical fibers, 12, 12a and a coherent optical fiber bundle 16. Optical fibers 12 and 12a deliver white light to the target and thus illuminate it while optical fiber 16 returns the image to a laser energy excluding means, 18, preferably a shutter or a filter (shown in FIG. 1). Excluding means 18 screens out the undesirable laser energy and therefore allows only the image of the target to continue on to the viewing port 20 where the physician can view the image. Alternatively, the image is coupled to a video camera 22. The camera transmits the image to a monitor 24 for viewing by the physician. The three optical fibers 12, 12a and 16 can be placed in a side-by-side arrangement, as illustrated in FIG. 3. Guidewire 32 is mounted on conduit 25 and housed within guidewire channel 33. Alternatively, guidewire 32a can be mounted outside of tube 14, in guidewire Channel 33a.

FIG. 3a illustrates an alternative embodiment of the invention. Optical fibers 112 can be positioned in a circle around optical fiber 116.

The material selected for wall 46 and for liquid 48 are selected in part to provide a high degree of internal reflection at the conduit surface. Specifically, wall 46 and liquid 48 are each transparent to laser energy which is conducted through the conduit while the index of refraction Nw of wall 46 is greater than the index of refraction Nf of liquid 48.

Further, the material for wall 46 is selected in part to provide structural strength as well as flexibility so that the liquid-filled conduit can be bent through curves of small radius without kinking or substantially distorting the cross-sectional geometry of the conduit 25. Preferably, wall 46 is made of a fluorinated ethylenepropyllene which is available commercially, for example as "FEP Teflon®" or a coating of a suitably low index of refraction optical media.

The light transmissive liquid 48 is injectable, transparent in visible light and in laser wavelengths, and has a refractive index greater than the refractive index of the sidewall 46. Suitable liquids include solutions of sugars such as mannitol, glucose, dextrose, and iodinated contrast media. Preferably such solutions have a refractive index of about 1.4. FEP Teflon® has a refractive index of about 1.33, thus, the ratio of their refractive indices is approximately 1.1, providing for substantially total internal reflection even at fairly steep angles of incidence. Preferably the surface of the conduit is smooth because surface roughness can produce unsatisfactory irregularities in angles of incidence.

Preferably, the liquid-filled conduit has an inside diameter of about 200 to 1500 micrometers. Preferably the thickness of the wall 46 is less than 0.010 inches. Such a conduit, 110 cm long, with a wall of FEP Teflon® and containing a sugar solution, can transmit from the distal end about 60% of laser energy at 480 nm, launched through a refractive index-matched lens or window into the proximal end from a laser. Preferably, laser energy is launched from the optical fiber into the fluid stream at a distance ranging from the tip of conduit 25 to a position about 20 cm withdrawn from the tip.

Figure 5:
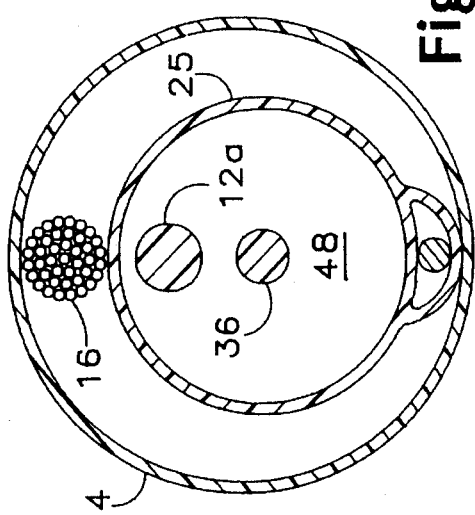
FIG. 5 is a cross-sectional view through the laser optical catheter taken along lines 5—5 in FIG. 4.
Figure 4:
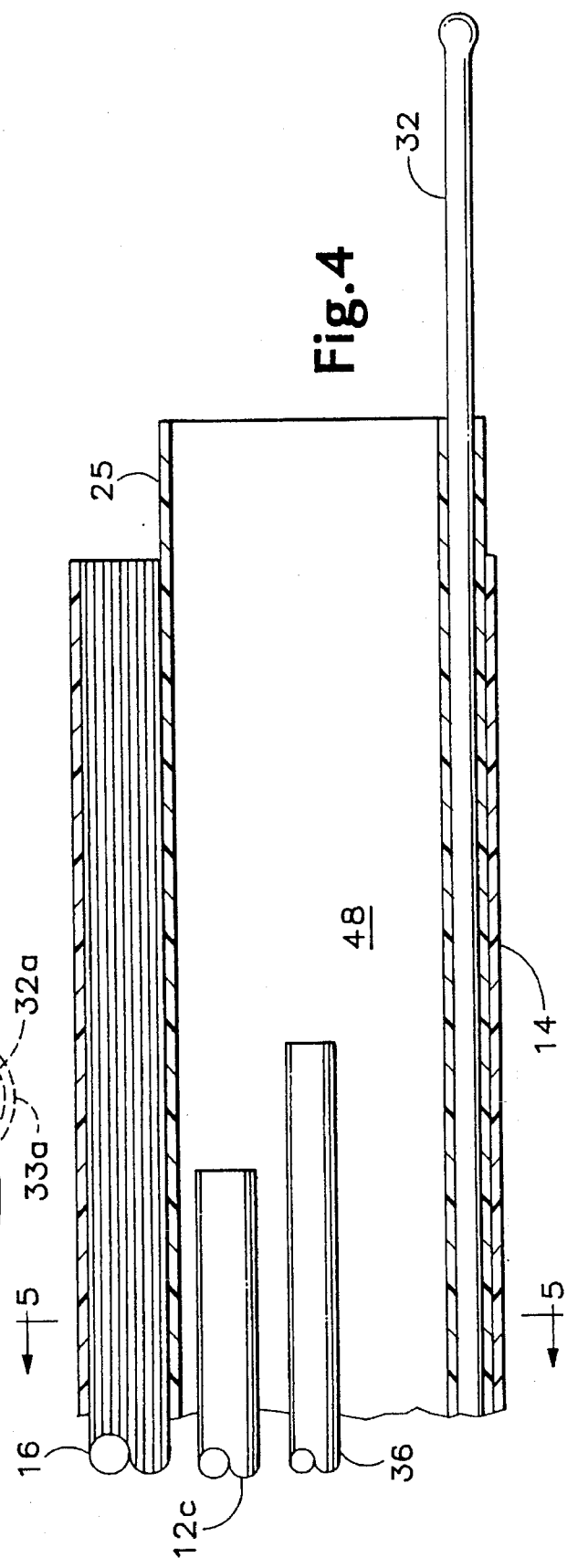
FIG. 4 is a sectional view, similar to FIG. 2, illustrating an alternative embodiment of the present invention.

An alternative embodiment of the present invention is illustrated in FIGS. 4 and 5. In this embodiment, optical fiber 12c launches white light into the liquid-filled conduit. The white light is wave-guided to the target by the liquid. The white light illuminates the target. The image of the illuminated target is transmitted back to be monitored by optical fiber 16. Laser energy is then launched into the liquid-filled conduit from optical fiber 36. The laser energy, as in other embodiments, is waveguided to the target by the liquid. This embodiment of the present invention has the advantage of eliminating additional optical fibers to transmit white light to illuminate the target. Without the additional optical fiber, the distal end of the tube is more flexible. Thus, this embodiment is particularly advantageous where great flexibility is required.

The tube is about 1–3 mm according to the diameter of the arterial lumen to be opened. Some materials that are optically suitable for use as a tube wall are structurally unsuitable or less suitable; that is, they are insufficiently flexible, or they collapse or kink or otherwise are distorted when they are bent through curves of small radius.

The liquid core laser scope operates generally as follows, with specific reference to its use for ablating arterial plaque occluding a coronary artery. Tube 14 is filled with liquid 48, and a source of liquid 26 is coupled to the proximal end of the liquid-filled tube 14. Liquid-filled tube 10 is introduced, distal end first through an opening in the skin and through the wall of a large artery such as the femoral artery, and is then passed translumenally under fluoroscopic guidance toward the site of the occlusion to be treated by laser energy, until the distal end resides in the lumen of the occluded artery and is directed toward the occlusion.

The progress of the tube can be monitored through the viewing port 20 without interruption or alternatively in monitor 24. Once the distal tip has reached the site and is directed toward the target, a further quantity of liquid can be introduced into the tube from the liquid source 26, causing some liquid to emerge from the distal end of the tube toward the target. Blood situated between the tube and the target can interfere with laser ablation of the plaque, because the blood absorbs nearly all wavelengths of laser energy better than does plaque. The liquid passing from the distal end of the tube displaces blood between the tube and the target removing this interference. As the emerging liquid displaces the blood, it provides a liquid channel distal to the distal end of the tube for passage of laser energy to the target, as best seen in FIG. 2. Moreover, the index of refraction of blood is about 1.34, sufficiently low relative to that of the liquid that the blood surrounding the liquid in this channel can form an effective light guide between the distal end of the tube and the target. Such a temporary liquid-core, liquid-clad light channel can be effective over distances in the order of about a centimeter for time intervals generally sufficient in the usual circumstances to complete the ablation and open the arterial lumen.

Then the laser energy source 34 is activated to produce laser energy having the desired wavelength and pulse duration and intervals. The progress of the laser ablation of the target can be observed through the viewing port 20 or video monitor 24, as the liquid serves not only as a light guide component but also to flush the blood away from the target. When the ablation has been completed, the liquid-filled tube is withdrawn.

A guide wire 32 can be used in the above-described procedure as desired, for example, if the walls of the arteries to be traversed by the tube themselves contain plaque formations that would interfere with the passage of the distal end of the tube during insertion.

A method to deflect the tip of conduit 25 to direct the fluid stream at eccentrically placed targets or down side branches may be desired and can be accomplished by persons skilled in the art. Alternatively, if the conduit 25 is eccentrically placed in flexible tube 14, a means for torquing or turning the tube 14 on its radius could be used to address lesions not directly in front of the tube 14.

Having described and illustrated the principles of the invention in a preferred embodiment thereof, it should be apparent that the invention can be modified in arrangement and detail without departing from such principles. I claim all modifications and variation coming within the spirit and scope of the following claims.

What is claimed is:

1. A liquid core laser optical scope for illuminating, viewing, and delivering laser energy to a site in a lumen of an animal or human body, the liquid core laser optical scope comprising:

a flexible tube having a distal end for insertion into the lumen;

a conduit housed within the tube;

means for coupling a flow of light transmissive liquid from an external source into the conduit for discharge from the conduit into the lumen at the distal end of the tube;

means defining a first light path through the tube for transmitting visible light from an external source through the tube to the distal end to illuminate the site in the lumen through the light transmissive fluid discharged into the lumen at the distal end of the tube;

means, disposed in the distal end of the tube, for imaging the illuminated site using light reflected back through the light transmissive fluid from the site in the lumen, and means defining a second light path through the tube and coupled to the imaging means for transmitting a visible image of the illuminated site from the site back through the tube to an external viewing port; and means defining a third light path for transmitting laser energy from an energy source into the conduit, the conduit having a sidewall capable of internally reflecting light into the liquid in the conduit so that the liquid waveguides the laser energy through the distal end of the conduit to the site the flow of light transmissive liquid discharging from the distal end of the tube to displace body fluids from the site and serve as an extension of said first, second and third light paths beyond said distal end to enable simultaneous optical illumination and imaging and laser energy irradiation of the illuminated site through a single temporary liquid core, liquid clad light channel with the distal end located at a position in the lumen spaced from the site.

2. A liquid core laser optical scope of claim 1 further including means in the second light path for excluding laser energy from the transmitted visible image.

3. A liquid core laser optical scope of claim 2 wherein the excluding means comprises a narrow band filter in the second light path.

4. A liquid core laser optical scope of claim 2 wherein the excluding means comprises a shutter in the second light path.

5. A liquid core laser optical scope of claim 1 wherein the fluid has an index of refraction greater than the index of refraction of the sidewall.

6. A liquid core laser optical scope of claim 5 wherein the fluid has an index of refraction of about 1.4 and the sidewall has an index of refraction of about 1.3.

7. A liquid core laser optical scope of claim 1 wherein the fluid is injectable, transparent in visible light and laser wavelengths.

8. A liquid core laser optical scope of claim 7 wherein the fluid is selected from the group consisting of one or more of mannitol, glucose, dextrose and iodinated contrast medium.

9. A liquid core laser optical scope of claim 1 further comprising guiding means including a guide conduit formed lengthwise in the tube.

10. A liquid core laser optical scope of claim 9 wherein the guiding means comprises a guidewire.

11. A liquid core laser optical scope according to claim 9 wherein the guiding means includes a deflectable tip.

12. A liquid core laser optical scope according to claim 9 wherein the guiding means includes a deflectable torsional rotation means extending along the tube for rotating the catheter to address eccentric lesions in the vessel.

13. A liquid core laser optical scope of claim 1 wherein the means defining a second light path comprises a coherent optical bundle.

14. A liquid core laser optical scope of claim 1 further comprising means extending along the tube for deflecting the flow of liquid from the distal end of the tube.

15. A method for ablating a site in a lumen of a human or animal body, using the liquid core laser optical scope of claim 1, comprising the steps of:
    inserting a catheter into the lumen, the catheter including the tube and conduit of claim 1;
    directing the catheter to the site;
    flowing the light transmissive fluid through the conduit and emitting said fluid in a single stream from the distal end of the catheter toward the site in the lumen;
    transmitting visible light to the site through the tube and lumen via the stream of light transmissive fluid;
    transmitting a visible image of the site from the site through the tube and lumen via the stream of light transmissive fluid; and
    simultaneously transmitting laser energy through the liquid filled conduit and lumen via the stream of light transmissive fluid to ablate the site.

16. A method of claim 15 wherein the site is selected from the group consisting of an atheromatous plaque, an atheroembolus, a thrombus, a blood clot, a lesion, a kidney stone, a gall stone, a tumor, and a polyp.

17. A method of claim 15 wherein the lumen is selected from the group consisting of an artery, a vein, a ureter, a common bile duct, a trachea, a bronchus, and a gastrointestinal tract.

18. A liquid core laser optical scope for illuminating, viewing, and delivering laser energy to a site in a lumen of a blood vessel of animal or human body while flushing blood away from the site to allow ease of angioscopic viewing, the liquid core laser optical scope comprising:
    a flexible tube having a proximal end and a distal end sized for insertion into the lumen;
    an external source of light transmissive liquid;
    a first conduit and a second conduit housed within the tube;
    means for coupling a flow of light transmissive liquid from the liquid source into a proximal end of the first conduit for discharge from the distal end thereof;
    an external source of visible light;
    means for coupling and transmitting visible light from the light source through the tube via one of the first and second conduits to the distal end thereof to illuminate the site;
    means for forming an optical image of the illuminated site disposed at the distal end of the tube;
    means for transmitting the optical image to the proximal end of the tube via the second conduit;
    means for coupling the transmitted image to a viewing apparatus, disposed at the proximal end of the scope;
    an external source of laser energy;
    means disposed at the proximal end of the first conduit for coupling laser energy from the energy source into the first conduit, the first conduit having a sidewall capable of internally reflecting light into the liquid in the conduit so that a liquid waveguide transmits the laser energy through the first conduit distal end to the site; and
    means for excluding the laser energy from the optical image transmitted to the proximal end of the scope;
    the flow of light transmissive liquid discharging in a single stream from the distal end of the tube to displace body fluids from the site and serve as a temporary liquid core, light clad light channel for transmitting the visible light and laser energy to the site from said distal end at a distance spaced from the site and the visible image from the site.

19. A liquid core laser optical scope of claim 18, wherein the means for forming an optical image of the illuminated site comprises a coherent optical bundle.

20. A liquid core laser optical scope of claim 19, wherein the means for forming an optical image of the illuminated site comprises a CCD imaging device.

* * * * *